United States Patent [19]

Nagy et al.

[11] Patent Number: 5,871,758

[45] Date of Patent: Feb. 16, 1999

[54] DUAL PHASE COSMETIC COMPOSITION

[75] Inventors: Adrienne Nagy, Waldwich, N.J.; Linda Najdek, E. Islip; Elena M. Ciriello, Yonkers, both of N.Y.; Henry Maso, Princeton, N.J.; Ralph Vitale, Centereach, N.Y.

[73] Assignee: E-L Management Corp., New York, N.Y.

[21] Appl. No.: 762,015

[22] Filed: Dec. 11, 1996

[51] Int. Cl.[6] .................................................. A61K 7/48

[52] U.S. Cl. ........................ 424/401; 514/23; 514/844; 514/845; 514/846

[58] Field of Search .................. 424/401; 514/844–896, 514/23

[56] References Cited

U.S. PATENT DOCUMENTS

| 4,335,103 | 6/1982 | Barker et al. | 424/59 |
| 4,438,095 | 3/1984 | Grollier et al. | 424/70 |
| 4,980,155 | 12/1990 | Shah et al. | 424/63 |
| 5,138,043 | 8/1992 | Polovsky et al. | 536/179 |
| 5,165,917 | 11/1992 | Zabotto et al. | 424/70 |
| 5,384,334 | 1/1995 | Polovsky et al. | 514/777 |
| 5,405,878 | 4/1995 | Ellis et al. | 424/28 |
| 5,454,494 | 10/1995 | Lechelle | 222/496 |
| 5,468,496 | 11/1995 | Touzan et al. | 424/40 |

*Primary Examiner*—Jyothsna Venkat
*Attorney, Agent, or Firm*—Karen A. Lowney, Esq.

[57] ABSTRACT

The present invention relates to a liquid dual phase cosmetic or pharmaceutical composition comprising an oil phase and an aqueous phase, the composition containing as a demixing agent a quaternary nitrogen-containing ether substituted alkoxylated alkyl glucoside. The compositions of the invention are particularly useful as makeup removers.

24 Claims, No Drawings

DUAL PHASE COSMETIC COMPOSITION

FIELD OF THE INVENTION

The present invention relates to cosmetic compositions. In particular, the invention relates to two-phase cleansing compositions which are particularly useful in makeup removal.

BACKGROUND OF THE INVENTION

Dual phase skin cosmetic compositions are currently very popular, in that they provide a broad range of cleansing/conditioning potential within a single product, and are also aesthetically appealing to the consumer. Typically, the dual phase product contains an aqueous phase and an oil phase, each adapted to removing a particular type of residue from the skin, or delivering a particular type of active. In a common use, for example, in a dual phase cleansing composition, the aqueous phase is designed to remove water-soluble material from the skin, while the oil phase is designed to remove oil-based, or "waterproof" material from the skin.

A number of factors must be considered in making a successful dual phase product. For example, in order to function properly, the two phases must be vigorously mixed, providing a temporary apparently homogeneous single phase product which delivers both phases to the region to be treated simultaneously. This typically means that the product must contain one or more surfactants or emulsifiers, which will render the two phases at least temporarily compatible during the mixing and application stage. Surfactants are also frequently useful in the removal of waterproof makeup. Unfortunately, many such emulsifiers are drying to the skin and/or are irritating to users, and in particular cannot be routinely used in the eye area.

On the other hand, however, it is also desirable that the two phases separate quickly after use, as the emulsified product has a cloudy appearance that is unappealing to consumers. After prolonged, continuous mixing of the two phases during regular use, the time it takes for the phases to separate becomes longer and longer, and the product rapidly loses its initially attractive appearance. Moreover, oil soluble actives may be unstable if in prolonged contact with the aqueous phase, and therefore, the amount of time spent in contact with the water phase should be minimized. As can readily be seen, these two aspects of the dual phase product, namely, the need for rapid and complete emulsification followed by rapid and complete separation, are at odds with each other, and to achieve both satisfactorily in a single product, in a way that is both cosmetically acceptable and attractive to the user, is often difficult. The present invention, however, provides a dual phase product in which the phases mix well and completely, and yet demixing is accomplished rapidly after use. Moreover, the product is non-irritating, and when used as a makeup remover, is highly successful in removing even the most difficult to remove oil-based cosmetics.

SUMMARY OF THE INVENTION

The present invention relates to a liquid dual phase cosmetic or dermatological composition comprising an aqueous phase and an oil phase, at least one of the phases containing as a demixing agent a quaternary nitrogen-containing ether substituted alkoxylated alkyl glucoside. In a preferred embodiment, the demixing agent is a compound having the formula

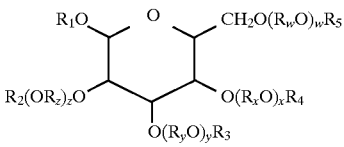

wherein
$R_1$ is alkyl, preferably $C_1$–$C_{18}$ alkyl;
each $R_w$, $R_x$, $R_y$, and $R_z$ is individually ethylene or propylene;
w, x, y and z provide an alkoxy molar substitution, MS defined by the average moles of alkoxy substituents represented by $R_{w-z}O$ in the formula as the average sum of w, x, y and z, per mole of the compound, of from about 1 to about 200; and
$R_2$, $R_3$, $R_4$ and $R_5$ are individually hydrogen or a quaternary nitrogen-containing group, each individually represented by the formula.

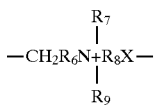

wherein:
R6 is C1–4 hydroxyalkylene;
R7, R8, R9 are individually or combined as C1–16 alkyl; and
X is an anion, preferably a halide, provided that at least one of R2, R3, R4 or R5 is a quaternary ammonium nitrogen-containing group.

The compositions of the invention are particularly useful when employed as a makeup remover, but may also be used for skin conditioning, or delivery of cosmetic or therapeutic active agents to the skin for the treatment and/or amelioration of various skin conditions.

DETAILED DESCRIPTION OF THE INVENTION

The demixing agents used in the present dual phase compositions are well-known in the art as cationic surfactants, and as such will lower the surface tension of water. They have been described generally as being useful in personal care products (U.S. Pat. Nos. 5,138,043, and 5,384,334) because skin and hair have an affinity for negatively charged skin and hair. They have also been shown to be useful as wetting agents in contact lens solution (U.S. Pat. No. 5,405,878). However, it has not been previously known that they can be used to facilitate rapid separation of a the phases in a two phase emulsion. In fact, given the surfactant character, it is quite surprising that they assist so efficiently in this separation. In addition to this function, however, these cationic glucosides have the additional advantage of being extremely mild, and non-irritating. In particular, they do not appear to cause any irritation when in contact with the eye, which cannot be said of many other cationic surfactants, such as benzalkonium chloride.

The glucoside demixing agents are made by processes known in the art, as for example, described in U.S. Pat. Nos. 5,138,043, and 5,384,334, the contents of which are incorporated herein by reference in their entirety. A preferred demixing agent is one in which each $R_w$, $R_x$, $R_y$, and $R_z$ is ethylene; particularly preferred is an ethoxylated glucose derivative, specifically lauryl methyl gluceth-10 hydroxypropyldimonium chloride. This particular material is available commercially under the tradename GLUCQUAT-100®, from Amerchol Corp., Edison, N.J.

The demixing agent, being water soluble, is preferably added to the aqueous phase of the composition, usually in an amount of from about 0.001–10%, preferably in an amount of about 0.05–5%. Dual phase compositions prepared with such a demixing agent. emulsify rapidly and uniformly upon vigorous shaking, and demulsify completely upon resting within approximately 5–20 minutes. The remainder of the composition is formulated depending on the nature of the desired end product. The ratio of the oil phase to aqueous phase is not critical, and can be varied in accordance with the type of product, but will generally be between 30:70 to 70:30, more preferably between 40:60 to 60:40. Most preferably, the aqueous phase is present as a higher weight per cent than the oil phase. The aqueous phase may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. As the oils can perform different functions in the composition, the specific choice is dependent on the purpose for which it is intended. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

The composition also may contain other cosmetically or therapeutically useful components. It may, for example, be desirable to incorporate other surfactants into the formulation, again depending on the intended purpose of the formulation, for example, as cleansing agents to assist in wetting skin, emulsifying oils or solubilizing soil on skin or as foaming agents. The surfactants employed may be any that are traditionally used for cosmetic or pharmaceutical purposes, and may be selected from nonionic, anionic, cationic or amphoteric surfactants, the identities of which are well known to those skilled in the art. Additional surfactants may be distributed in either or both of the phases of the formulation, and selection is limited only by a given surfactant's compatibility with the phase into which it is incorporated, and by the location to which the composition is to be applied. Other potentially useful components of the formulation include emollients, humectants, fragrances, preservatives, and buffers. Such materials are routinely used in cosmetic products, and listings of appropriate materials can be found, for example in the International Cosmetic Ingredients Handbook, Third Edition, 1996 (CTFA).

As noted above, the formulation can also be used for therapeutic or quasi-therapeutic purposes, and therefore may also comprise useful active ingredients, for the purposes of treating both the skin and hair. Useful active ingredients include, but are not limited to antioxidants, antimicrobials, sunscreens, analgesics, anesthetics, anti-acne agents, antidandruff agents, antidermatitis agents, antipruritic agents, anti-inflammatory agents, antihyperkeratolytic agents, antidry skin agents, antiperspirants, antipsoriatic agents, antiseborrheic agents, hair conditioners and hair treatment agents, antiaging agents, antiwrinkle agents, antihistamine agents, skin lightening agents, depigmenting agents, wound-healing agents, vitamins, corticosteroids, tanning agents, or hormones. The location of the active in the formulation is determined by its solubility and/or stability in either oil or water.

The formulations of the present invention are useful for a variety of purposes, including skin or hair cleansers, skin or hair treatment products, sunscreen or suntanning products, and the like. In a particularly preferred embodiment, however, the composition is used for removing makeup. As already noted, the cationic glucoside demixing agents, because of their mildness, are eminently well-suited to being employed in a product which is usable around the eye. When combined with an appropriate group of additional components, particularly in the oil phase, the resulting makeup remover successfully cleans skin surfaces, particularly eyes and lips, of even the most transfer-resistant of currently used cosmetics, while remaining gentle and non-irritating to the user.

In this preferred embodiment, the oil phase preferably contains a combination of both volatile and non-volatile oils. In a particularly preferred embodiment, the amount of volatile used is considerably higher than that of the non-volatile oils; for example, in a typical formulation, the volatile oil will be present in an amount of about 30–70%, preferably about 40–60%, of the total composition, and the non-volatile oil in an amount of about 0.1–10%, preferably about 0.2–5%. In one preferred embodiment, the volatile oil portion contains a combination of a volatile silicone and a volatile paraffin, in amounts of from about 10–60% volatile silicone, and 5–40% volatile paraffin, by weight of the total composition. The nonvolatile portion of the oil phase is preferably a non-volatile silicone. In a particularly preferred embodiment, the oil phase contains a blend of oils comprising a low molecular weight cyclic silicone at 25–40% by weight, a volatile $C_{16}$ isoparaffin at 15–30% by weight, and the non-volatile silicone at 0.1–1% by weight. A preferred non-volatile silicone is dimethicone.

In this preferred embodiment, it may be desirable to provide an additional small amount of surfactant in the oil phase to facilitate removal of the cosmetic residue from the skin. The amount of surfactant added is preferably no more than 5%, and more preferably is in the range of 0.1–1%. The surfactant may be of any type, i.e., anionic, nonionic, cationic or amphoteric; however, if the makeup remover is intended for use in the eye area, it is preferred that the surfactant should be a mild surfactant, such as LIPO-PEG-2DL or disodium cocoaamphoidaceatate (Miranol).

The invention is further illustrated in the following non-limiting examples:

EXAMPLES

1. The following illustrates a formulation of the present invention:

| MATERIAL | PERCENT BY WEIGHT |
|---|---|
| Cyclomethicone | 30 |
| Isohexadecane | 25 |
| Sodium chloride | 0.5 |
| Dimethicone | 0.25 |
| Glucquat 100 ® | 0.05 |
| Benzyl alcohol | 0.1 |
| Purified water | Q.S. to 100% |

The components are combined as follows: the oil phase components, cyclomethicone, isohexadecane, and dimethicone are mixed with the benzyl alcohol, and the water phase components, sodium chloride, Glucquat 100® and water are mixed together. First the oil phase is added to the selected container, then the water phase is added.

What we claim is:

1. A dual phase liquid cosmetic or pharmaceutical composition comprising an aqueous phase and an oil phase, each phase being separate from the other except when mixed at the time of use, the composition containing as a demixing agent an effective amount of a quaternary nitrogen-containing ether substituted alkoxylated alkyl glucoside of formula I:

$$R_1O \diagdown \diagup O \diagdown CH_2O(R_wO)_wR_5 \quad (I)$$
$$R_2(OR_z)_zO \diagup \diagdown O(R_xO)_xR_4$$
$$O(R_yO)_yR_3$$

wherein $R_1$ is $C_1$–$C_{19}$ alkyl;

each $R_w$, $R_x$, $R_y$, and $R_z$ is individually ethylene or propylene;

w, x, y and z provide an alkoxy molar substitution, the molar, substitution defined by the average moles of alkoxy substituents represented by $R_{w-z}O$ in the formula as the average sum of w, x, y and z, per mole of the compound, of from about 1 to about 200; and $R_2$, $R_3$, $R_4$ and $R_5$ are individually hydrogen or a quaternary nitrogen-containing group, each individually represented by the formula:

$$\begin{array}{c} R_7 \\ | \\ -CH_2R_6N+R_8X- \\ | \\ R_9 \end{array}$$

wherein:

R6 is C1–4 hydroxyalkylene;

R7, R8, R9 are individually or combined as C1–16 alkyl; and

X is an anion, provided that at least one of R2, R3, R4 or R5 is a quaternary ammonium nitrogen-containing group, in an amount of from about 0.001–10% by weight of the total composition, and in which the oil phase comprises a volatile oil in an amount of about 30–70% and a non-volatile oil, in an amount of 0.1–10%, by weight of the total composition.

2. The composition of claim 1 wherein, in the compound of formula (I), each of $R_w$, $R_x$, $R_y$, and $R_z$ is ethylene.

3. The composition of claim 1 in which the compound is lauryl methyl gluceth-10 hydroxypropyldimonium chloride.

4. The composition of claim 1 in which the oil phase and aqueous phase are present in a ratio of from about 30:70 to 70:30, by weight.

5. The composition of claim 1 in which the aqueous phase and oil phase are present in a ratio of from about 40:60 to 60:40, by weight.

6. A liquid dual phase makeup removal composition comprising an oil phase and an aqueous phase, each phase being separate from the other except when mixed at the time of use, the composition containing as a demixing agent, an effective amount of a compound of the formula (I):

$$R_1O \diagdown \diagup O \diagdown CH_2O(R_wO)_wR_5 \quad (I)$$
$$R_2(OR_z)_zO \diagup \diagdown O(R_xO)_xR_4$$
$$O(R_yO)_yR_3$$

wherein $R_1$ is alkyl;

each $R_w$, $R_x$, $R_y$, and $R_z$ is individually ethylene or propylene;

w, x, y and z provide an alkoxy molar substitution, the molar substitution defined by the average moles of alkoxy substituents represented by $R_{w-z}O$ in the formula as the average sum of w, x, y and z, per mole of the compound, of from about 1 to about 200; and $R_2$, $R_3$, $R_4$ and $R_5$ are individually hydrogen or a quaternary nitrogen-containing group, each individually represented by the formula:

$$\begin{array}{c} R_7 \\ | \\ -CH_2R_6N+R_8X- \\ | \\ R_9 \end{array}$$

wherein:

R6 is C1–4 hydroxyalkylene;

R7, R8, R9 are individually or combined as C1–16 alkyl; and

X is an anion, provided that at least one of R2, R3, R4 or R5 is a quaternary ammonium nitrogen-containing group, in an amount of from about 0.001–10% by weight of the total composition, and in which the oil phase comprises a volatile oil in an amount of about 30–70% and a non-volatile oil, in an amount of 0.1–10%, by weight of the total composition.

7. The composition of claim 6 wherein, in the compound of Formula (I), each of $R_w$, $R_x$, $R_y$, and $R_z$ is ethylene.

8. The composition of claim 7 in which the compound is lauryl methyl gluceth-10 hydroxypropyldimonium chloride.

9. The composition of claim 8 in which the compound is present in an amount of from about 0.001–10%.

10. The composition of claim 9 in which the compound is present in an amount of from about 0.5–5%.

11. The composition of claim 6 in which the volatile oil comprises both a volatile silicone and a volatile isoparaffin.

12. The composition of claim 11 in which the volatile silicone is cyclomethicone and the volatile isoparaffin is a $C_{16}$ isoparaffin.

13. The composition of claim 6 in which the non-volatile oil comprises a non-volatile silicone.

14. The composition of claim 13 in which the silicone is dimethicone.

15. A liquid dual phase makeup removal composition comprising an oil phase and an aqueous phase, the composition containing as a demixing agent, an effective amount of lauryl methyl gluceth-10 hydroxypropyldimonium chloride, in an amount of from about 0.001–10% by weight of the total composition, and in which the oil phase comprises a volatile oil in an amount of about 30–70% and a non-volatile oil, in an amount of 0.1–10%, by weight of the total composition.

16. The composition of claim 15 in which the volatile oil comprises a volatile silicone and a volatile paraffin.

17. The composition of claim 16 in which the non-volatile oil comprises a non-volatile silicone.

18. The composition of claim 17 which comprises about 25–40% of a cyclic silicone, 15–30% of a $C_{16}$ isoparaffin, and 0.1–1% of a non-volatile silicone.

19. The composition of claim 18 in which the cyclic silicone is cyclomethicone, the isoparaffin is isohexadecane, and the non-volatile silicone is dimethicone.

20. The composition of claim 19 which comprises an additional surfactant in an amount of no greater than 5%.

21. The composition of claim 20 in which the additional surfactant is present in an amount of from about 0.1–1%.

22. The composition of claim 21 in which the oil phase and aqueous phase are present in a ratio of about 40:60 to 60:40.

23. The composition of claim 1 in which the anion is a halide.

24. The composition of claim 6 in which the anion is a halide.

* * * * *